United States Patent [19]
Cathrein et al.

[11] Patent Number: 5,364,563
[45] Date of Patent: Nov. 15, 1994

[54] POWDERED AQUEOUS CAROTENOID DISPERSIONS

[75] Inventors: Ernst Cathrein, Aesch; Hermann Stein, Liestal; Hansjörg Stoller, Reinach; Klaus Viardot, Riehen, all of Switzerland

[73] Assignee: Hoffmann-La Roche Inc., Nutley, N.J.

[21] Appl. No.: 187,355

[22] Filed: Jan. 25, 1994

Related U.S. Application Data

[63] Continuation of Ser. No. 16,483, Feb. 10, 1993, abandoned, which is a continuation of Ser. No. 551,830, Jul. 12, 1990, abandoned.

[30] Foreign Application Priority Data

Jul. 25, 1989 [CH] Switzerland ............... 2778/89

[51] Int. Cl.$^5$ ............... A61K 31/015; A61K 9/14; A61K 47/44; A23L 1/275
[52] U.S. Cl. ............... 252/311; 252/312; 426/540; 426/73; 424/502; 514/724
[58] Field of Search ............... 426/540.73, 96, 98; 252/306, 311, 312; 424/489, 502

[56] References Cited

U.S. PATENT DOCUMENTS

| | | | |
|---|---|---|---|
| 2,861,891 | 11/1958 | Bauernfiend et al. | 426/540 |
| 3,110,598 | 11/1963 | Muller et al. | 426/540 |
| 4,522,743 | 6/1985 | Horn et al. | 252/311 |
| 4,726,955 | 2/1988 | Horn et al. | 426/73 |
| 4,844,934 | 7/1989 | Lueddecke et al. | 426/540 |

FOREIGN PATENT DOCUMENTS

| | | |
|---|---|---|
| 0239086 | 3/1987 | European Pat. Off. |
| 0278284 | 1/1988 | European Pat. Off. |
| 1211911 | 3/1966 | Germany |
| 2943267 | 5/1981 | Germany ............... 426/540 |

*Primary Examiner*—Robert L. Stoll
*Assistant Examiner*—John M. Covert
*Attorney, Agent, or Firm*—George M. Gould; William H. Epstein; Catherine A. Picut

[57] ABSTRACT

A novel process for producing powdered carotenoid preparations, in which a suspension of a carotenoid in a high-boiling oil is brought into contact with superheated steam during a maximum period of 30 seconds, and subsequently emulsified the liquified solution of said carotenoid in oil produced by said contact with superheated steam in an aqueous solution of a colloid and then spraying and drying said emulsion to a powder.

7 Claims, 1 Drawing Sheet

POWDERED AQUEOUS CAROTENOID DISPERSIONS

This is a continuation of application Ser. No. 08/016,483 filed Feb. 10, 1993, now abandoned, which is a continuation of application Ser. No. 07/551,830 filed Jul. 12, 1990, now abandoned.

BACKGROUND OF THE INVENTION

It has been suggested that e.g. β-carotene is effective as a prophylactic against cancerous illnesses. β-Carotene as well as other carotenoids such as e.g. lycopene, bixin, zaxanthin, cryptoxanthin, lutein, canthaxanthin, astaxanthin, β-apo-8'-carotenal, β-apo-12'-carotenal as well as esters of hydroxy- and carboxy-containing compounds of this group, e.g. the lower alkyl esters, preferably the methyl ester and ethyl ester, have, moreover, acquired a considerable significance as colorants or color-imparting agents for foodstuffs or also as feed additives.

However, carotenoids are substances which are insoluble in water, have high melting points and, moreover, are also sensitive to heat and oxidation.

In the case of e.g. β-carotene these properties, especially the water-insolubility, give rise to an extremely poor bioavailability from pharmaceutical dosage forms such as, for example, tablets, capsules etc. which contain this carotenoid. The aforementioned properties are, moreover, an obstacle to a direct use of the crystalline materials for the coloring of aqueous foodstuffs, as feed additives or also for use as a source of vitamin A, since the materials in this form are absorbed only poorly or give only a poor coloring effect. The above-mentioned properties of carotenoids are especially disadvantageous in the coloring of aqueous media, since it is extremely difficult, because of their water-insolubility, to achieve a homogeneous or sufficiently intense coloring effect.

Various processes for the manufacture of such preparations are already known from the literature, but these are associated with in each case more or less great disadvantages. Thus, for example, from German Patent No. 1 211 911 it is known to manufacture carotenoid preparations by dissolving a carotenoid in a carotenoid solvent, emulsifying the solution in an aqueous solution of a protective colloid and subsequently removing the solvent from this emulsion. The disadvantage of this process resides in the fact that chlorinated hydrocarbons are preferably used as the solvent and their removal is extremely expensive from the industrial point of view. Furthermore, for example, it is known from European Patent No. 65 193 to manufacture carotenoid preparations by dissolving a carotenoid in a non-chlorinated volatile water-miscible organic solvent at temperatures between 50° and 200° C. within a period of less than 10 seconds, precipitating the carotenoid in colloid-dispersed form from the solution obtained by mixing with a solution of a colloid and subsequently removing the solvent. Here also an organic solvent must therefore be removed, which again is expensive from the industrial point of view.

There accordingly exists a need for a process for the manufacture of powdered carotenoid preparations which is carried out without the use of organic solvents and which are readily dispersible in aqueous media and which, moreover, - in the case of β-carotene - are suitable for the manufacture of pharmaceutical dosage forms having good bioavailability of the active substance.

SUMMARY OF THE INVENTION

The present invention is concerned with a novel process for the manufacture of colloid-dispersed carotenoid preparations and with the thus-manufactured preparations themselves. The preparations manufactured in accordance with the invention are useful, depending on the carotenoid which is used, not only for the manufacture of pharmaceutical administration forms, but also for the coloring of foodstuffs and as feed additives.

By means of the process in accordance with the invention it is now possible to avoid the described disadvantages and to obtain carotenoid preparations having the desired properties which preparations do not contain conventionally used organic solvents.

DETAILED DESCRIPTION

Figure 1:
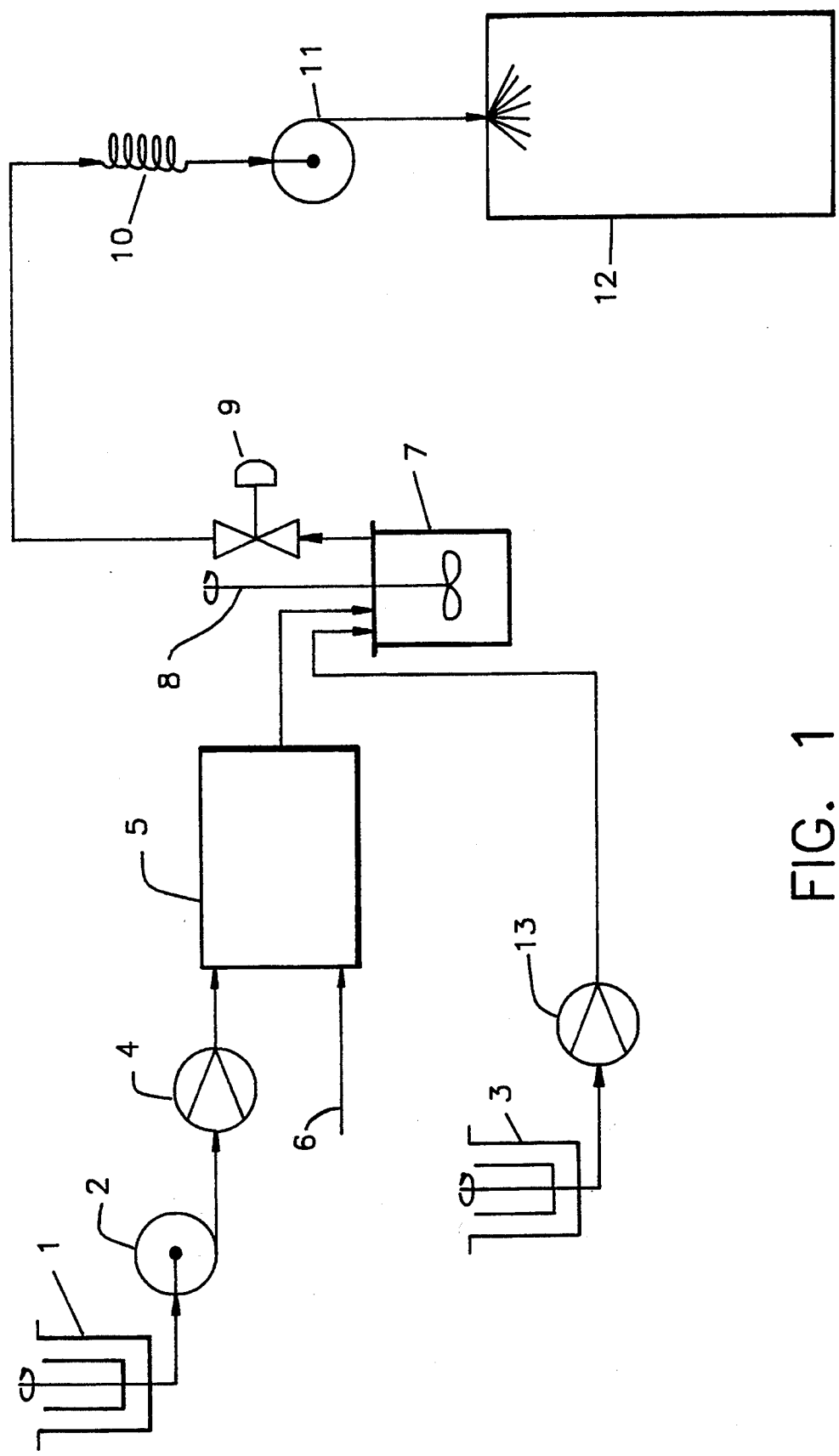
FIG. 1 sets forth the scheme for converting a carotenoid in a high boiling oil into powdered particles with the carotenoid dispersed in a colloid.

The process in accordance with the invention for the manufacture of colloid-dispersed carotenoid preparations in the form of dry powder comprises bringing a suspension of a carotenoid in a high-boiling oil into contact with superheated steam during a maximum period of 30 seconds to dissolve the carotenoid in said oil, emulsifying this solution in an aqueous solution of a colloid and subsequently spraying and drying this emulsion to form a powder wherein the carotenoid is dispersed in the colloid.

The term "carotenoid" embraces in the scope of the present invention all representatives of this class of substances which are known and which usually come into consideration for the coloring of foodstuffs and as feed additives, especially the compounds mentioned earlier. These carotenoids can be used alone or in the form of mixtures depending on the purpose of use or depending on the desired coloring. In accordance with this invention any conventional high boiling oil can be utilized especially the triglycerides of fatty acids having about 8-22 carbon atoms, preferably about 16-20 carbon atoms such as, for example, edible oils, e.g. groundnut oil, corn oil, sunflower oil, hardened coconut oil etc. Furthermore, the term high boiling oil include mixtures of oils such as mixtures of triglycerides having 8-22 carbon atoms, especially those mixtures of triglycerides of saturated fatty acids having 8-12 carbon atoms such as e.g. products which are available under the brand names MIGLYOL 812 or MYRITOL 318 etc.

Such oils generally have a boiling point of at least about 200° C. and serve in the process in accordance with the invention as "solvent/carrier material" for the carotenoids which are used.

The suspension of a carotenoid in a high-boiling oil can be effected in a manner known per se, for example by mixing in a stirring kettle. When the suspension obtained has particles which are too coarse, it can be converted by milling, e.g. in a ball mill, into a suspension in which about 90% of the particles have a size of less than 15 μ. The production of this suspension is conveniently effected under an inert gas such as, for example, argon or nitrogen. Because the carotenoids, as mentioned earlier, are sensitive to oxidation, an antioxidant may be conveniently added to this suspension. As such antioxidants there come into consideration especially tocopherols, particularly dl-α-tocopherol, BHT (tert.-butylhydroxytoluene) as well as BHA (tert.-butylhydroxyanisole) and the like. The concentration of the suspension depends on the respective carotenoid which is used and also on the proposed use of the end product. These concentrations generally lie between about 10–50 wt. %.

The bringing into contact of the suspension with the super heated steam can be effected in a suitable mixer, e.g. in an inline mixer. Thereby, the suspension is dosed continuously into the mixer and simultaneously the superheated steam is fed in. The temperature of the steam is conveniently from about 180° C. to about 230° C., preferably from about 190° to about 210° C., and the pressure conveniently lies between about 10 bar and about 30 bar, preferably at about 12 bar to about 19 bar. In the case of e.g. β-carotene, the steam upon entry into the mixer preferably has a temperature of about 200°–205° C., with a pressure of about 16 bar, measured at the steam inlet. The amount of steam is regulated in such a manner that the temperature of the mixture at the outlet of the mixer is about 180°–190° C. The use of superheated steam in accordance with the process of this invention caused the carotenoid suspended in the oil to dissolve and form a solution.

In order to prevent too great losses of carotenoids at the high temperatures used during the treatment with superheated steam and to control any isomerizations - e.g. trans-β-carotene to cis-β-carotene - as far as possible, the contact time of superheated steam with the carotenoid suspension in the mixer is a maximum of 30 seconds. However, this contact time is preferably a maximum of 15–20 seconds or at a maximum of 5–10 or 1–2 seconds, and especially below 0.5 second. This can be regulated especially by the size of the mixer and by varying the amount of throughput (carotenoid suspension+steam). Moreover, in order to lower the temperature rapidly, the resulting oil-water- carotenoid mixture should be emulsified immediately in an aqueous matrix of a protective colloid. An aqueous solution of a colloid and an emulsifier is conveniently used as the matrix. Any conventional colloid can be used in accordance with this invention. As colloids there especially come into consideration all substances which can normally be used as protective colloids such as, for example, gelatin, gum arabic, milk and vegetable proteins, carbohydrates such as sugar, starch and starch derivatives etc., as well as mixtures thereof. However, a mixture of gelatin and sugar is preferably used. As emulsifiers there come into consideration the usual products which are permitted for pharmaceutical preparations or for foodstuffs such as, for example, sorbitan derivatives, glycerol monostearate, citric acid esters and especially ascorbyl palmitate, etc..

The emulsification can be effected in a manner known per se such as, for example, by stirring or by means of ultrasonics etc. In the thus-obtained emulsion the average particle size of the internal phase (oil in water) is from about 0.5–1 μ. This emulsion is subsequently cooled to about 50°–70° C. and finely dispersed in a second homogenization step, i.e. to particle sizes of the internal phase of about 0.1–0.3 μ. This homogenization can again be effected in a manner known per se. At the conclusion of this second homogenization step the emulsion is then sprayed in a manner known per se and converted into a dry preparation.

The dry carotenoid preparation thus produced is a powder. The particles of this powder contain the colloid having dispersed therein a solution of the carotenoid dissolved in the high boiling oil. These particles are free of organic solvents, particularly those solvents used for dissolving carotenoids, especially volatile water-miscible organic solvents.

The entire process in accordance with the invention can be carried out not only continuously, but also batchwise.

The process in accordance with the invention can be carried out, for example, as follows in an apparatus as shown in the scheme of FIG. 1.

A suspension of a carotenoid in a high-boiling oil is prepared in a stirring kettle (1), optionally with the addition of an antioxidant. The suspension is then milled in a ball mill (2) until about 90% of the particles have a size of less than 15μ. Subsequently, this suspension is dosed by means of a pump (4) into the mixer (5). Simultaneously, superheated steam is fed into the mixer via the steam inlet (6). The amount of steam is regulated such that the desired temperature prevails at the outlet of the mixer. The residence time of the carotenoid suspension in the mixer is a maximum of 30 seconds. Parallel thereto, an aqueous matrix is prepared in a heatable kettle (3) from a protective colloid and an emulsifier and is pumped via a pump (13) into the homogenization kettle (7). Herein the matrix is then emulsified with the oil-water carotenoid mixture from the mixer (5), cooled and homogenized. The emulsion obtained is subsequently subjected to a pressure release to atmospheric pressure by means of a valve (9), then cooled in a heat exchanger (10) and finely dispersed in a homogenizer (11). Subsequently, the dispersion obtained is sprayed in a spraying tower (12) and dried.

EXAMPLE 1

1) 48 kg of cryst. β-carotene were suspended in a stirring kettle (1) in a mixture of 6.2 kg of dl-α-tocopherol and 54.9 kg of MIGLYOL 812 (triglyceride of saturated fatty acids of average chain-length, especially $C_8$ and $C_{10}$). This suspension was milled in a ball mill (2) so that 90% of the particles were <15μ.

2) 30.8 kg of sugar and 109.5 kg of gelatin were dissolved in 213.8 kg of water in a second stirring kettle (3). The pH value was adjusted to 7.0 with sodium hydroxide solution. Now, 5.5 kg of ascorbyl palmitate were introduced and the pH value was held constant at 7.0 until the ascorbyl palmitate had dissolved.

3) 20–22 kg/h of the β-carotene suspension produced according to 1) were dosed into the inline mixer (5) by means of a geared pump (4). Simultaneously, the mixer was fed with steam (amount about 6 kg/h) of 16 bar (6) and a temperature of 200° C. The amount of steam was regulated in such a manner that the temperature at the outlet of the inline mixer was 185°–186° C. The pressure of the steam in front of the regulating valve was 30 bar. The residence time of the β-carotene suspension in the inline mixer at a temperature of 185°–186° C. was <0.5 seconds. Immediately thereafter the hot homogeneous mixture of β-carotene, MIGLYOL 812, tocopherol and water was mixed in the homogenization kettle (7) with the warm (about 48° C.) matrix solution produced according to 2). The matrix solution was dosed into the homogenization vessel (7) via a pump (13) in an amount of 186 kg/h. Thereby, the temperature of the β-carotene/MIGLYOL/water mixture dropped suddenly from 185°–186° C. to 74°–76° C., whereby there formed initially a coarse-particled emulsion which was improved by treatment in the homogenizer (8). The average residence time in the homogenization kettle (7) was 0.3 minute. The emulsion was then removed continuously via a pressure-retaining valve (9) and a tubular condenser (10) and thereby cooled to about 55°–60° C. The pressure in the homogenization kettle (7) was 15–16 bar.

The thus-obtained B-carotene emulsion was subsequently homogenized in the homogenizer (11) to a particle size of the internal phase of 0.25 μm. Subsequently, the viscous liquid was converted into a stable dry powder by spraying into a bed of starch (12) and subsequently drying. The β-carotene content of the dry powder was 7.0%, with 70% being present as trans-β-carotene.

EXAMPLE 2

β-carotene powders were manufactured in an analogous manner to Example 1 using as the oils corn oil, groundnut oil and, respectively, hardened coconut oil:

|  | Expt. 1) | Expt. 2) | Expt. 3) |
| --- | --- | --- | --- |
| β-Carotene suspension |  |  |  |
| - Cryst. β-carotene | 22.0 kg | 22.0 kg | 41.0 kg |
| - dl-α-Tocopherol | 2.9 kg | 2.9 kg | 4.7 kg |
| - Groundnut oil | — | 75.1 kg | — |
| - Corn oil | 75.1 kg | — | — |
| - Hardened coconut oil | — | — | 54.3 kg |
| Matrix |  |  |  |
| - Water | 160.0 kg | 120.0 kg | 163.6 kg |
| - Sugar | 16.4 kg | 16.4 kg | — |
| - Gelatin | 58.4 kg | 58.4 kg | 90.0 kg |
| - Ascorbyl palmitate | 5.85 kg | 1.3 kg | 3.0 kg |
| - Sorbitol solution (70%) | — | — | 43.4 kg |
| Feed amounts inline mixer |  |  |  |
| - β-Carotene suspension | 22.0 kg/h | 19.5 kg/h | 21.0 kg/h |
| -continued |  |  |  |
|  | Expt. 1) | Expt. 2) | Expt. 3) |
| - Steam | 6.0 kg/h | 6.0 kg/h | 6.0 kg/h |
| - Temperature at the outlet of the inline mixer | 185–186° C. | 186° C. | 185–186° C. |
| - Residence time in the inline mixer | <0.5 sec. | <0.5 sec. | <0.5 sec. |
| Homogenization kettle |  |  |  |
| - Matrix | 70.0 kg/h | 56.0 kg/h | 143.8 kg/h |
| - Temperature in the homogenization vessel | 86–88° C. | 88° C. | 82–84° C. |
| - Residence time in the homogenization kettle | 0.6 min. | 0.75 min. | 0.7 min. |
| β-Carotene powder |  |  |  |
| - Content of β-carotene | 6.7% | 7.5% | 7.5% |
| - trans-β-Carotene | 70.0% | 68.0% | 69.2% |

We claim:

1. A process for producing a powdered carotenoid preparation comprising forming a suspension of a carotenoid in a high boiling oil without the presence of an organic solvent, contacting said suspension with superheated steam for a maximum period of thirty seconds to form a solution of said carotenoid in said oil, emulsifying said solution in an aqueous solution of a colloid and thereafter spraying and drying said emulsion to form said powder.

2. The process of claim 1 wherein said carotenoid is β-carotene.

3. The process of claim 2 wherein said oil has a boiling point of at least 200° C.

4. The process of claim 3 wherein said oil is a triglyceride of a saturated fatty acid.

5. The process of claim 4 wherein the contact time between the carotenoid suspension and superheated steam is a maximum of 15–20 seconds.

6. The process of claim 5 wherein said maximum contact time is less than 0.5 seconds.

7. The process of claim 3 wherein said oil is groundnut oil, corn oil, hardened coconut oil, or sunflower oil.

* * * * *